(12) United States Patent
Mann

(10) Patent No.: US 6,783,781 B2
(45) Date of Patent: Aug. 31, 2004

(54) METHOD OF STABILIZING FRUIT-CONCENTRATE POWDERS

(76) Inventor: Douglas G. Mann, 1435 E. Venice Ave, #257, Venice, FL (US) 34292

(\*) Notice: Subject to any disclaimer, the term of this patent is extended or adjusted under 35 U.S.C. 154(b) by 215 days.

(21) Appl. No.: 09/996,051

(22) Filed: Nov. 28, 2001

(65) Prior Publication Data

US 2002/0102336 A1 Aug. 1, 2002

Related U.S. Application Data

(60) Provisional application No. 60/253,631, filed on Nov. 29, 2000.

(51) Int. Cl.[7] .................. A23L 1/053; A23L 1/034
(52) U.S. Cl. .............. 426/74; 426/519; 426/573; 426/590; 426/599; 426/640
(58) Field of Search .................. 426/74, 590, 599, 426/573, 519, 640

(56) References Cited

U.S. PATENT DOCUMENTS

| | | |
|---|---|---|
| 3,640,784 A | 2/1972 | Yancik et al. |
| 4,034,764 A | 7/1977 | Rainer et al. |
| 4,129,134 A | 12/1978 | Hind et al. |
| 4,143,666 A | 3/1979 | Rainer et al. |
| 4,435,439 A | 3/1984 | Morris |
| 4,477,481 A | 10/1984 | Eisenhardt, Jr. et al. |
| 4,664,920 A * | 5/1987 | Saleeb et al. .......... 426/74 |
| 4,743,384 A | 5/1988 | Lu et al. |
| 4,764,374 A | 8/1988 | Grimberg |
| 4,828,839 A | 5/1989 | Stemmle et al. |
| 4,834,988 A | 5/1989 | Karwowski et al. |
| 4,965,252 A | 10/1990 | Kuhrts |
| 5,085,880 A | 2/1992 | Devic |
| 5,124,162 A * | 6/1992 | Boskovic et al. .......... 426/96 |
| 5,304,620 A | 4/1994 | Holtmeyer |
| 5,357,636 A | 10/1994 | Dresdner, Jr. et al. |
| 5,445,839 A * | 8/1995 | Hagiwara et al. ........ 426/270 |
| 5,567,439 A | 10/1996 | Myers et al. |
| 5,587,172 A | 12/1996 | Cherukuri et al. |
| 5,616,344 A | 4/1997 | Battist et al. |
| 5,622,719 A | 4/1997 | Myers et al. |
| 5,645,853 A | 7/1997 | Winston et al. |
| 5,658,956 A | 8/1997 | Martin et al. |
| 5,692,302 A | 12/1997 | Martin et al. |
| 5,720,347 A | 2/1998 | Audibert et al. |
| 5,728,400 A | 3/1998 | Battist et al. |
| 5,733,577 A | 3/1998 | Myers et al. |
| 5,851,552 A | 12/1998 | Myers et al. |
| 5,851,553 A | 12/1998 | Myers et al. |
| 5,853,762 A | 12/1998 | Myers et al. |
| 5,866,163 A | 2/1999 | Myers et al. |
| 5,871,781 A | 2/1999 | Myers et al. |
| 5,885,594 A | 3/1999 | Nilsen et al. |
| 5,895,664 A | 4/1999 | Cherukuri et al. |
| 5,958,380 A | 9/1999 | Winston et al. |
| 5,965,162 A | 10/1999 | Fuisz et al. |
| 6,231,866 B1 | 5/2001 | Mann |

FOREIGN PATENT DOCUMENTS

GB     1 070 060     5/1967

OTHER PUBLICATIONS

Vinson, Joe A., et al., Phenol Antioxidant Quantity and Quality in Foods: Fruits, *J. Agric. Food Chem.*, 2001, vol. 49, pp. 5315–5321, American Chemical Society, US.

Hejzlar, L., et al., The Effect of Prophylactic Administration of Cranberry Extract (Swiss CRAN–MAX™ 7500 mg) on the Occurence of Recurring Infections of the Urinary Tract (4 pages).

Poduska, H., Swiss Max Brusinsky 7500 mg (Cran–Max™)—Initial Trial (3 pages), Biovet Impex Co., 1999–2000.

Risch, Sara J., Encapsulation and Controlled Release of Food Ingredients, Chapter 18—Review of Patents for Encapsulation and Controlled Release of Food Ingredients, ACS Symposium Series 590, 1995, pp. 196–203, American Chemical Society.

Http://www.foodnavigator.com, Carob Fibre Hits the Shelves, FoodNavigator Newsletter, Nov. 14, 2001 (2 pages).

Http://www.foodnavigator.com, Fruit Extracts Fit the Bill, FoodNavigator Newsletter, Nov. 14, 2001 (2 pages).

\* cited by examiner

*Primary Examiner*—Helen Pratt
(74) *Attorney, Agent, or Firm*—Mueller and Smith, LPA

(57) ABSTRACT

A method and formulation for stabilizing fruit concentrate powders, using stabilizing substrates such as magnesium salt, citric acid, and gum, in a vacuum drying system.

19 Claims, No Drawings

METHOD OF STABILIZING FRUIT-CONCENTRATE POWDERS

CROSS-REFERENCE TO RELATED APPLICATIONS

This application claims priority under 35 U.S.C. §119(e) to U.S. Provisional Patent Application 60/253,631 filed Nov. 29, 2000, the entirety of which is incorporated by reference herein.

FIELD OF THE INVENTION

The present invention is directed to a method and formulation to improve and stabilize the nonvolatile components of a fruit concentrate powder and to create low-hygroscopic dried fruit concentrate powder.

DESCRIPTION OF THE PRIOR ART

There are numerous methods of fixing (a term used synonymously herein with "stabilizing") food ingredients in edible substrates. Materials commonly used as substrates include dextrins and hydrophilic colloids, e.g., gum arabic, gelatin, and maltodextrine. However, many of these materials result in a loss of flavor components (a "low fix") and an increase in the caloric value of the end product due to the caloric content of the substrate itself and create a product that is highly hygroscopic. This characteristic substantially affects the flow capability of these ingredients. In addition, conventional methods require substantially more substrate to fix the end product. Thus, the fruit solids are distributed to a much larger amount of substrate, reducing flavor, taste, and scent.

In general, fixation is a process whereby non-volatile flavor, fragrance, and/or color components are complexed to a substrate and the components are protected from oxidative degradation. The substrate (i.e., the "fixative" or "fixing agent") is thoroughly mixed with the matter to be fixed, and the mixture is then dried to yield the fixed product. The mixture is dried using any number of conventional means, such as by spray drying, drum drying, or freeze drying. However, vacuum drying results in a non-hygroscopic, dry, flowable powder.

U.S. Pat. No. 4,664,920 to Saleeb et al., describes several examples of fixing food ingredients, including fruit juice concentrates and oils, in magnesium salt substrates. The method uses as a fixative an aqueous solution of magnesium salts of edible mono-, di, or tri-basic acids, such as acetic, lactic, propionic, adipic, fumaric, malic, succinic, phosphoric, and citric acids. However, the resulting end product contains a relatively high magnesium content. For example, when fixing orange and lemon juice concentrates, the method of Saleeb et al. yields spray-dried formulations containing from 5 to 15% by weight magnesium fixative.

Thus, it would be advantageous to have a formulation that results in higher yields of fruit solids in the dried powder and far lower magnesium content in the dried powder when spray dried, and in a low hygroscopic powder when vacuum dried, and could deliver a highly concentrated nutraceutical to the body when ingested.

SUMMARY OF THE INVENTION

The present invention is directed to a method of fixing fruit comprising blending the fruit with an aqueous solution comprising magnesium hydroxide in amount no greater than 5 percent by weight, an organic acid component and a stabililizer; and drying the fruit to produce either a non- or low-hygroscopic, dried fruit powder.

The present invention is also directed to a method of fixing a fruit juice concentrate comprising blending the fruit juice concentrate with an aqueous solution comprising magnesium hydroxide in amount less than 5 percent by weight, an organic acid component selected from the group consisting of citric acid and ascorbic acid, in an amount less than 5 percent by weight, and a stabililizer selected from the group consisting of guar gum and gum arabic in an amount sufficient to maintain the stability of the final product; and drying the fruit juice concentrate to produce a low- or non-hygroscopic, dried fruit powder.

The present invention is also directed to fruit ingredients produced by these methods.

The present invention is drawn to a fruit derivative stabilizing formula and methodology that preserves fruit juice concentrate at a high level of fruit solids while encapsulating flavor and color in a magnesium-based fixative present in reduced concentrations. For purposes of brevity only, the following discussion is limited to the preferred embodiment, the production of cranberry powder. However, the invention is not so limited; the process can be applied with equal success using any fruit juice or fruit juice concentrate starting material.

The method uses magnesium salts, preferably magnesium salts of citric or ascorbic acid, and a gum (arabic or guar), to stabilize (i.e., "fix") the nonvolatile components and preserve the desirable properties of fruit concentrates. The preferred fruit concentrates are cranberry, blueberry, bilberry, elderberry, and chokeberry. The formulation increases the flow of product through all types of drying apparatuses, and yields a product having a higher retention of starting fruit solids than other methods. The method also uses far less magnesium salt than prior art methods and thus produces a fruit product with a smaller concentration of magnesium compounds.

Fruit concentrates are sold today largely as food ingredients rather than as dietary supplements and have greatly varying degrees of fruit solids from 50%–90%. The present method yields an end product containing at least 91%–94% fruit solids, with less than 4% magnesium content.

The method yields a low or substantially low hygroscopic, dried concentrate, increases the flow and yield of the drying process, and retains a high proportion, typically between 85% and 95% solids in the final product depending on the fruit dried.

The present formulation also functions beneficially with enhanced fruit fiber. The method may further include the step of mixing the liquid mixture prior to drying with natural cranberry fibers from which the juice has already been expressed. The soluble dietary fiber ingredient acts as a natural delivery system of the fixed fruit juice solids to the absorption/digestive tissues of the gut upon ingestion. Alternatively, the natural fiber-product can be dry blended with dried fruit concentrate to obtain similar results.

DETAILED DESCRIPTION OF THE INVENTION

The invention is a method of fixing fruit juices, particularly cranberry, blueberry, bilberry, elderberry, and chokeberry juice concentrates, comprising mixing the fruit juice or fruit juice concentrate with a fixative blend containing magnesium hydroxide, an organic acid, such as citric and/or ascorbic acid, and guar gum or gum arabic to yield a liquid mixture, and then drying the liquid mixture to yield a low hygroscopic, powdered fruit juice composition containing fruit juice solids and a reduced amount of magnesium salt fixative. The process maintains a high proportion of original fruit juice solids while efficiently stabilizing the spray-dried fruit juice powder product.

The fruit juice concentrate can be prepared according to methods known to the art. Reference is made to applicant's own U.S. Pat. No. 6,231,866, the disclosure of which is incorporated herein in its entirety, for a description of fruit juice concentrate preparations and an expanded list of fruits, vegetables and herbs, which may be used in the present invention.

The present formulation combines magnesium salts, stabilizers such as gum arabic, and organic acids such as citric or ascorbic acid with fruit juice in proportions which achieve a dried, fixed, low hygroscopic end product containing significantly less magnesium in the dried product than has been described in the prior art.

Reference is made to U.S. Pat. No. 4,664,920 to Saleeb, which is incorporated herein by reference for a description of magnesium salts useful in the present invention. The preferred magnesium salt is magnesium hydroxide present in the formulation in an amount less than 5 percent by weight, and preferably between about 2 and 4 percent by weight.

The present formulation includes a stabilizer to produce the desired body, texture and stability to the product. Stabilizers are preferably derived from natural sources such as plants and the like, although some of the stabilizers may be modified in order to render them stable and food grade functional. Examples of stabilizers which can be utilized in the product include guar gum, gum arabic, locust bean gum, pectin, seaweed, xanthan gum, carrageenan, an alginate, cellulose gums, modified starches, gelatin and/or maltodextrins, with guar gum and gum arabic being preferred. Preferably, the stabilizer is selected to maintain the stability and the consistency of the product.

The organic acid may be any suitable acid, such as citric or ascorbic acid, which are preferred in accordance with the present formulation. The organic acid is added in an amount typically less than 5 percent and preferably between about 2 and 4 percent by weight. For a more acidic stabilizer formula, the level of organic acid may be increased up 10 percent or higher and the level of fruit concentrate may be proportionately decreased. Unless otherwise indicated, percentages appearing below refer to weight percentage of the subject formulation.

The product is then dried. This can be done on drying racks in a conventional dehydrator or by vacuum drying means, or by any other means for drying known to the art of food and pharmaceutical processing, such as spray drying. Low-temperature drying means (not to exceed about 140° F.) are greatly preferred. It is preferred that the moisture content of the dried mixture be no more than about 3% by weight.

Stabilized fruit concentrates are achieved with less than 5% (by weight) of either magnesium salt or citric/ascorbic acid. The mechanism by which the magnesium salt is able to fix fruit juice at reduced salt concentrations is unknown. While not being held to any particular mechanism, it is believed that the fixative capacity of the present formulation may be due to the chemistry between the particular acids present in fruit juices, and cranberry juice in particular, the magnesium cation, and the citrate or ascorbate anion.

Magnesium ions in combination with citric acid, form organo-metallic compounds, possibly magnesium acid citrates, which hold or fix the color-bearing and flavor-bearing anthocyanin and related molecules of cranberries in a way not completely understood. At least as applied to cranberries, the juice of cranberries contains unknown quantities of higher complex compounds of citric acid, as well as anthocyanins, oligomeric proanthocyanidins, and other flavinol compounds. At least in cranberry, a stabilizing effect is achieved with a lower magnesium ion concentration. Consequently, the invention results in a significant reduction in the magnesium content of the end product, while still yielding a stabilized, low or non-hygroscopic dried cranberry product. The invention thus provides a high-efficiency process for fixing cranberries, this high efficiency being directly translatable into increased economic gains over previous methods.

EXAMPLES

The following Examples are included solely as an aid to more clearly illustrate the invention. The Examples do not limit the invention disclosed herein in any fashion.

Example 1

To provide a formula for a 50-gallon (c. 400 lb) batch of stabilized cranberry concentrate, magnesium hydroxide, citric acid, and an amount of guar gum for binding purposes are combined with cranberry concentrate as follows:

| | | |
|---|---|---|
| cranberry concentrate (50 brix) | 62.8% | 251.2lbs |
| water USP | 26.7% | 120.0lbs |
| citric acid monohydrate USP | 3.9% | 15.6lbs |
| magnesium hydroxide USP | 3.3% | 13.2lbs |
| Gum Arabic(Tic Gum) | 3.3% | 13.2lbs |

The stabilizer liquid is formed by thoroughly mixing at room temperature and gradually increasing the solution to 120° F. the magnesium hydroxide, citric acid and gum arabic. Then, the cranberry concentrate slurry is slowly added to the stabilizer liquid and blended for 5 minutes. For a more acidic stabilizer formula, the level of citric acid may be increased to 10% or higher and the level of cranberry concentrate may be proportionately decreased.

The liquid mixture is then spray-dried using a conventional spray-drying apparatus. Analysis of the dried product shows it to contain approximately 93%–96% of the beginning solids weight. Normal spray drying returns only average between 83%–85% of the beginning solid weight. The product is pink-red in color, free-flowing, and substantially low hygroscopic.

Example 2

To produce a stabilized chokeberry concentrate, the following are combined

| | | |
|---|---|---|
| chokeberry concentrate | 66.0% | 220.0 g |
| water USP | 25.0% | 78.0 g |
| magnesium hydroxide USP | 2.0% | 6.70 g |
| ascorbic acid (Vitamin C, USP) | 2.0% | 6.85 g |
| Gum arabic | 5.0% | 17.6 g |

A chokeberry concentrate used was found to have a pH of 4.79, which corresponded to 18.42 mg/mil (or 1.84%) magnesium hydroxide required to neutralize the concentrate.

Therefore, a stabilized concentrate was produced with lower percentages of ascorbic acid and magnesium hydroxide, and an increased percentage of concentrate.

Water plus magnesium hydroxide and ascorbic acid are first blended well. Then, this mixture is added to the chokeberry concentrate with thorough mixing for five minutes. The pH of the stabilized preparation is 7.1.

The liquid mixture then blended with an amount of quar gum for binding purposes and is then spray-dried as described above. The product is free flowing and substantially non-hygroscopic and contains less than 2% magnesium.

Example 3

Fifty pounds of the above described magnesium substrate was placed in a vacuum rotary dryer. Five hundred pounds of 50 brix cranberry concentrate was then slowly added to the substrate. The powders were rotated slowly under vacuum and heated until all the measured concentrate was consumed. The process yielded 300 pounds of non-hygroscopic fruit powder.

It is understood that the invention is not confined to the particular construction and arrangement of parts herein illustrated and described, but embraces such modified forms thereof as come within the scope of the claims.

What is claimed is:

1. A method of fixing fruit, comprising the steps of:
   (a) blending the fruit with an aqueous solution comprising magnesium hydroxide in an amount no greater than 5% by weight, an organic acid component and a stabilizer, and
   (b) drying the fruit to produce a low or non-hygroscopic, dried fruit powder.

2. The method of claim 1 wherein the fruit is selected from the group of fruits consisting of cranberry, blueberry, bilberry, elderberry and chokeberry.

3. The method of claim 1 wherein the fruit is in the form of fruit juice.

4. The method of claim 1 wherein the fruit is in the form of fruit juice concentrate.

5. The method of claim 1 wherein the organic acid component is selected from the group consisting of citric acid and ascorbic acid.

6. The method of claim 1 wherein the organic acid component is present in an amount between 2 and 4% by weight.

7. The method of claim 1 wherein the stabilizer is selected from the group consisting of guar gum and gum arabic.

8. The method of claim 1 wherein the drying is effected by freeze drying, spray drying, vacuum drying or rack drying.

9. A dried fruit powder, which comprises
   (a) a fruit;
   (b) no greater than 5% by weight of magnesium hydroxide;
   (c) an organic acid component; and
   (d) a stabilizer.

10. The dried fruit powder of claim 9, wherein:
    (a) between about 91% and 94% by weight is said fruit;
    (c) between about 2% and 4% by weight is said organic acid component; and
    (d) said stabilizer is present in an amount sufficient to maintain the stability of the final product.

11. The dried fruit powder of claim 10, wherein said organic acid component ranges from between about 2% and 4%.

12. The dried fruit powder of claim 9, wherein said organic acid component is one or more of citric acid or ascorbic acid, and said stabilizer is one or more of guar gum or gum arabic.

13. The dried fruit powder of claim 9, wherein said fruit is one or more of cranberry, blueberry, bilberry, elderberry and chokeberry.

14. The method of claim 1, wherein fruit fiber is blended in step (a) prior to said diving step (b).

15. A method of fixing a fruit juice concentrate, comprising the steps of:
    (a) blending the fruit juice concentrate with an aqueous solution comprising magnesium hydroxide in an amount between about 2% and 4% by weight, an organic acid component selected form the group consisting of citric acid and ascorbic acid, in an amount less than 5% by weight, and a stabilizer selected from the group consisting of guar gum and gum arabic in an amount sufficient to maintain the stability of the final product; and
    (b) drying the fruit juice concentrate to produce a low or non-hygroscopic, dried fruit powder.

16. The method of claim 15, wherein said organic acid component ranges from between about 2% and 4%.

17. The method of claim 15, wherein fruit fiber is blended in step (a) prior to said drying step (b).

18. The method of claim 15, wherein said fruit is one or more of cranberry, blueberry, bilberry, elderberry and chokeberry.

19. The method of claim 16, wherein said fruit is one or more of cranberry, blueberry, bilberry, elderberry and chokeberry.

* * * * *